United States Patent [19]

Rashbrook

[11] 4,203,888
[45] May 20, 1980

[54] POLYESTER FILMS

[75] Inventor: Robert B. Rashbrook, Hatfield, England

[73] Assignee: ICI Americas Inc., Wilmington, Del.

[21] Appl. No.: 651,779

[22] Filed: Jan. 23, 1976

Related U.S. Application Data

[63] Continuation of Ser. No. 488,232, Jul. 12, 1974, abandoned.

[30] Foreign Application Priority Data

Mar. 5, 1974 [GB] United Kingdom ................. 9823/74

[51] Int. Cl.² .............................................. C08K 5/51
[52] U.S. Cl. ......................... 260/45.7 P; 260/45.7 PS
[58] Field of Search ..................... 260/45.7 P, 45.7 PS

[56] References Cited

U.S. PATENT DOCUMENTS

| | | | |
|---|---|---|---|
| 2,520,690 | 8/1950 | Barrett | 106/177 |
| 3,061,571 | 10/1962 | Heberling | 260/45.7 P |
| 3,300,440 | 1/1967 | Prevorsek | 260/47.7 PS |

FOREIGN PATENT DOCUMENTS

| | | |
|---|---|---|
| 2214372 | 11/1973 | Japan . |
| 2416472 | 11/1973 | Japan . |
| 4018772 | 11/1973 | Japan . |
| 1405983 | 9/1975 | United Kingdom . |

*Primary Examiner*—Melvyn I. Marquis
*Attorney, Agent, or Firm*—John M. Sheehan

[57] ABSTRACT

Oriented flame retardant films are made from linear polyester compositions containing an aryl diphosphate.

6 Claims, No Drawings

POLYESTER FILMS

This is a continuation of application Ser. No. 488,232 filed July 12, 1974 and now abandoned.

This invention relates to oriented films of linear polyesters. Such films are of use for a variety of applications and for some such applications, especially decorative, it is desirable that the film be flame retardant. Effective flame retardant compounds for linear polyesters are organic phosphorus compounds, particularly phosphates.

However, the processing of linear polyesters into films normally involves the application of high processing temperatures e.g. in the extrusion stage, and many organic phosphates, such as triphenyl phosphate, are relatively volatile at such temperatures. This gives rise to a considerable loss of the phosphate during manufacture of the film with the result that either insufficient flame retardant properties are donated to the film or an uneconomic amount of phosphate has to be employed.

Furthermore the volatility of the phosphates gives rise to the emission of acrid, possibly toxic, fumes during production of the film therby creating a health hazard.

It is also desirable that the flame retardant does not adversely affect the colour of the film.

We have found that this use of a particular class or orgainc phosphates overcomes these difficulties.

Accordingly we provide an oriented film made from a composition comprising a linear polyester and from 5 to 20% by weight, based on the weight of the polyester, of an organic diphosphate of the formula:

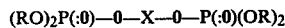

$(RO)_2P(:O)—O—X—O—P(:O)(OR)_2$ wherein X is a divalent aryl hydrocarbon radical, which may be halogen substituted, in which each free valence stems from an aryl necleus and R represents a mononuclear aryl hydrocarbon radical, which may be halogen substituted.

U.S. Pat. No. 2,520,090, the disclosure of which is incorporated herein by reference, describes the manufacture and use of such diphosphates. U.S. pat. No. 2,520,090 states that the diphosphates can be used a plasticisers in cellulose derivatives and other materials such as synthetic rubbers, polyvinyl chloride and copolymers of vinyl chloride with other vinyl monomers. It is stated that the plasticising compounds are adapted to impart flame resistant properties to the cellulose derivatives to which they are added and which are characterised by being relatively non-volatile.

The group X is preferably selected from phenylene, diphenylene, diphenylene sulphone and 2,2 bis phenylene propane groups. Preferably the meta, or 3,3', or para, or 4,4',groups are utilised, i.e. 3,3' or 4,4' diphenylene, 3,3' or 4,4' diphenylene sulphone, 2,2 bis 3-phenylene propane or 2,2 bis 4-phenylene propane groups. The aryl group R is preferably phenyl, cresyl, xylenyl, or t-butyl phenyl. Particularly preferred are phenyl groups. The groups X and/or R may be halogen substituted, by for example chlorine or bromine, but preferably are not halogen substituted.

Polyesters that may be used include the condensation products of one or more dicrboxylic acids or their lower alkyl diesters, for example terephthalic acid, isophthalic acid, phthalic acid, 2,5-, 2,6- or 2,7-naphthalene dicarboxylic acid, succinic acid, sebacic acid, adipic acid, azelaic acid, bibenzoic acid, hexahydroterephthalic acid, or bis-p-carboxy phenoxy ethane, with one or more glycols for example ethylene glycol, 1,3 propandeiol, 1,4 butanediol, neopentyl glycol, or 1,4 cyclohexane di methanol. The preferred polyester is polyethylene terephthalate or polyethylene-1,2-diphenoxy ethane-4,4'-dicarboxylate.

The composition should contain between 5 and 20% by weight of the diphosphate, based on the weight of the polyester. If less than 5% by weight is used, little flame retardant effect is exhibited while if more than 20% by weight is utilised to properties of the resultant film are too adversely affected. Preferably the amount of diphosphate is between 8 and 15% by weight of the polyester.

The oriented films are normally fabricated by extruding a melt of the polyester to which the diphosphate has been added through a film forming die, quenching the extruded film and the orienting the film by drawing it uniaxially or biaxially. Normally, after orienting, the film is heated to effect crystallisation while restraining, or premitting only little, shrinkage, hence heat setting the film. The film is preferably extruded through a slit die to produce a flat film.

The film may be coated as is well known in the art and also it may be metallised.

The films are of a particular utility for decorative applications such as metallised film for artificial christmas trees and garlands, for electrical applications, e.g. transformer insulation and printed circuits, as a laminating film, as furniture cladding film, and as a base for insulating and pressure sensitive adhesive tapes.

EXAMPLE

Terephthalic acid and ethylene glycol were esterified using a slight excess of ethylene glycol over equimolar quantities in the presence of a softening point stabiliser. The reaction was carried out under a pressure of 2.80 atmospheres at 235°–240° C.

At the end of this reaction about 0.05% by weight, based on the weight of terephthalic acid used, of antimony trioxide catalyst was added together with a trivalent phosphorous stabiliser and about 0.1% by weight based on the weight of the terephthalic acid used of a suitable filler. This mixture was heated to 290° C. with stirring with reduction of pressure of 1 mm of mercury to remove glycol. When the viscosity of the reaction mixture had risen to about 4000 poise (corresponding to an intrinsic viscosity of 0.70 dl/g as measured on a 1% by weight solution of the polymer in o-chlorophenol at 25° C.) 12% by weight, based on the weight of the polyester, of tetraphenyl metaphenylene diphosphate was added and stirred in. There was a drop in viscosity, and the polycondensation was carried further to raise viscosity back to about 4000 poise.

The polymer was then converted to biaxially drawn heat set films fo a range of thicknesses. During the filming process almost no fumes were noticed. Color of the film was almost unaffected by the addition of the diphosphate. The film was self-extinguishing after removal of the source of ignition.

Similar results were obtained using tetraphenyl 2,2 bis(4-phenylene)propane diphosphate in place of tetraphenyl metaphenylene diphosphate.

By way of comparison when triphenyl phosphate was used in place of the diphosphate, severe fuming occurred during the production of the film and the fumes evolved were acrid and toxic.

I claim:

1. A polyester composition which comprises a linear polyester as the main component and from 5 to 20% by weight based on the polyester, of an organic diphosphate of the formula:

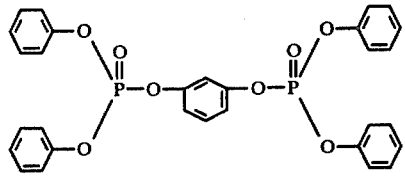

2. A polyester composition according to claim 1, in which the concentration of the organic diphosphate is between 8% and 15% by weight based on the polyester.

3. A polyester composition according to claim 1, in which the main component is polyethylene terephthalate.

4. An oriented film made from a composition comprising a linear polyester and from 5 to 20% by weight based on the polyester, of an organic diphosphate of the formula:

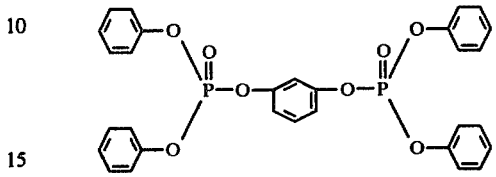

5. An oriented film according to claim 4, in which the concentration of the organic diphosphate is between 8% and 15% by weight based on the polyester.

6. An oriented film according to claim 4, in which the polyester is polyethylene trephthalate.

* * * * *

UNITED STATES PATENT AND TRADEMARK OFFICE
CERTIFICATE OF CORRECTION

PATENT NO. : 4,203,888
DATED : May 20, 1980
INVENTOR(S) : Robert B. Rashbrook

It is certified that error appears in the above-identified patent and that said Letters Patent are hereby corrected as shown below:

[73] "ICI Americas Inc., Wilmington, Del." should read -- Imperial Chemical Industries Limited, London, England --.

Column 1, line 27, "or" should read -- of --.

Column 1, line 64, "dicrboxylic" should read -- dicarboxylic --.

Column 2, line 3, "pandeiol" should read -- panediol --.

Signed and Sealed this

Fifth Day of August 1980

[SEAL]

Attest:

SIDNEY A. DIAMOND

Attesting Officer

Commissioner of Patents and Trademarks